(12) United States Patent
Schnarr et al.

(10) Patent No.: US 11,992,707 B2
(45) Date of Patent: May 28, 2024

(54) 3D IMAGING WITH SIMULTANEOUS TREATMENT AND NON-TREATMENT IMAGING BEAMS

(71) Applicant: ACCURAY INCORPORATED, Sunnyvale, CA (US)

(72) Inventors: Eric Schnarr, McFarland, WI (US); Calvin R. Maurer, San Jose, CA (US); Rich Holloway, Chapel Hill, NC (US); Jacob D. Shea, Cross Plains, WI (US); Charles Brandon Frederick, Raleigh, NC (US)

(73) Assignee: Accuray Incorporated, Sunnyvale, CA (US)

( * ) Notice: Subject to any disclaimer, the term of this patent is extended or adjusted under 35 U.S.C. 154(b) by 0 days.

(21) Appl. No.: 18/133,464

(22) Filed: Apr. 11, 2023

(65) Prior Publication Data
US 2023/0249000 A1    Aug. 10, 2023

Related U.S. Application Data

(63) Continuation of application No. 17/364,527, filed on Jun. 30, 2021, now Pat. No. 11,638,838.

(51) Int. Cl.
*A61N 5/00* (2006.01)
*A61N 5/10* (2006.01)

(52) U.S. Cl.
CPC ......... *A61N 5/1067* (2013.01); *A61N 5/1031* (2013.01); *A61N 5/1038* (2013.01); *A61N 5/1045* (2013.01); *A61N 5/1078* (2013.01)

(58) Field of Classification Search
CPC .................................. A61N 5/00; A61N 5/10
See application file for complete search history.

(56) References Cited

U.S. PATENT DOCUMENTS

| | | | |
|---|---|---|---|
| 5,673,300 | A | 9/1997 | Reckwerdt et al. |
| 6,618,467 | B1 | 9/2003 | Ruchala et al. |
| 2005/0185758 | A1 | 8/2005 | Bruder et al. |
| 2007/0041499 | A1* | 2/2007 | Lu .................... A61N 5/1048 378/65 |
| 2009/0110145 | A1 | 4/2009 | Lu et al. |

(Continued)

FOREIGN PATENT DOCUMENTS

| | | | |
|---|---|---|---|
| WO | 2008013598 | A2 | 1/2008 |
| WO | 2018183748 | A1 | 10/2018 |

(Continued)

OTHER PUBLICATIONS

PCT International Search Report and Written Opinion from related PCT Application No. PCT/US2022/032235, mailed on Sep. 19, 2022 (13 pages).

*Primary Examiner* — Dani Fox

(74) *Attorney, Agent, or Firm* — Womble Bond Dickinson (US) LLP

(57) ABSTRACT

A radiation treatment session is initiated to deliver a therapeutic radiation beam from a therapeutic radiation source to a target. One or more X-ray radiation sources are caused to deliver an imaging radiation beam from the one or more X-ray radiation sources through the target to one or more X-ray detectors to acquire imaging data associated with the target during therapeutic radiation beam delivery. One or more volumetric images are constructed using the acquired imaging data.

20 Claims, 9 Drawing Sheets

(56) References Cited

U.S. PATENT DOCUMENTS

| | | |
|---|---|---|
| 2010/0316259 A1 | 12/2010 | Liu et al. |
| 2011/0112351 A1 | 5/2011 | Fordyce, II et al. |
| 2012/0230462 A1 | 9/2012 | Robar et al. |
| 2018/0345042 A1 | 12/2018 | Voronenko et al. |
| 2018/0369611 A1 | 12/2018 | Owens et al. |
| 2020/0258231 A1 | 8/2020 | Li et al. |

FOREIGN PATENT DOCUMENTS

| | | |
|---|---|---|
| WO | 2018187618 A1 | 10/2018 |
| WO | 2018226257 A1 | 12/2018 |

* cited by examiner

3D IMAGING WITH SIMULTANEOUS TREATMENT AND NON-TREATMENT IMAGING BEAMS

CROSS-REFERENCE TO RELATED APPLICATIONS

This application is a continuation of co-pending U.S. patent application Ser. No. 17/364,527 filed on Jun. 30, 2021, and this application is specifically incorporated by reference herein in its entirety.

TECHNICAL FIELD

The present disclosure relates to three-dimensional (3D) imaging with simultaneous treatment and non-treatment imaging beams.

BACKGROUND

In radiation treatment, a radiation delivery system may utilize imaging for patient alignment, motion tracking, and verification of dose delivered to the subject. 3D volumetric images are the most useful for visualizing and tracking the relative positions of tumors (i.e., the target of radiotherapy treatments) and surrounding organs. Images constructed from data acquired at the same time that therapeutic radiation is being delivered provide the most relevant view of what the subject looks like at the moment the radiation is delivered.

BRIEF DESCRIPTION OF THE DRAWINGS

The present disclosure will be understood more fully from the detailed description given below and from the accompanying drawings of various implementations of the disclosure.

DETAILED DESCRIPTION

Figure 1A:
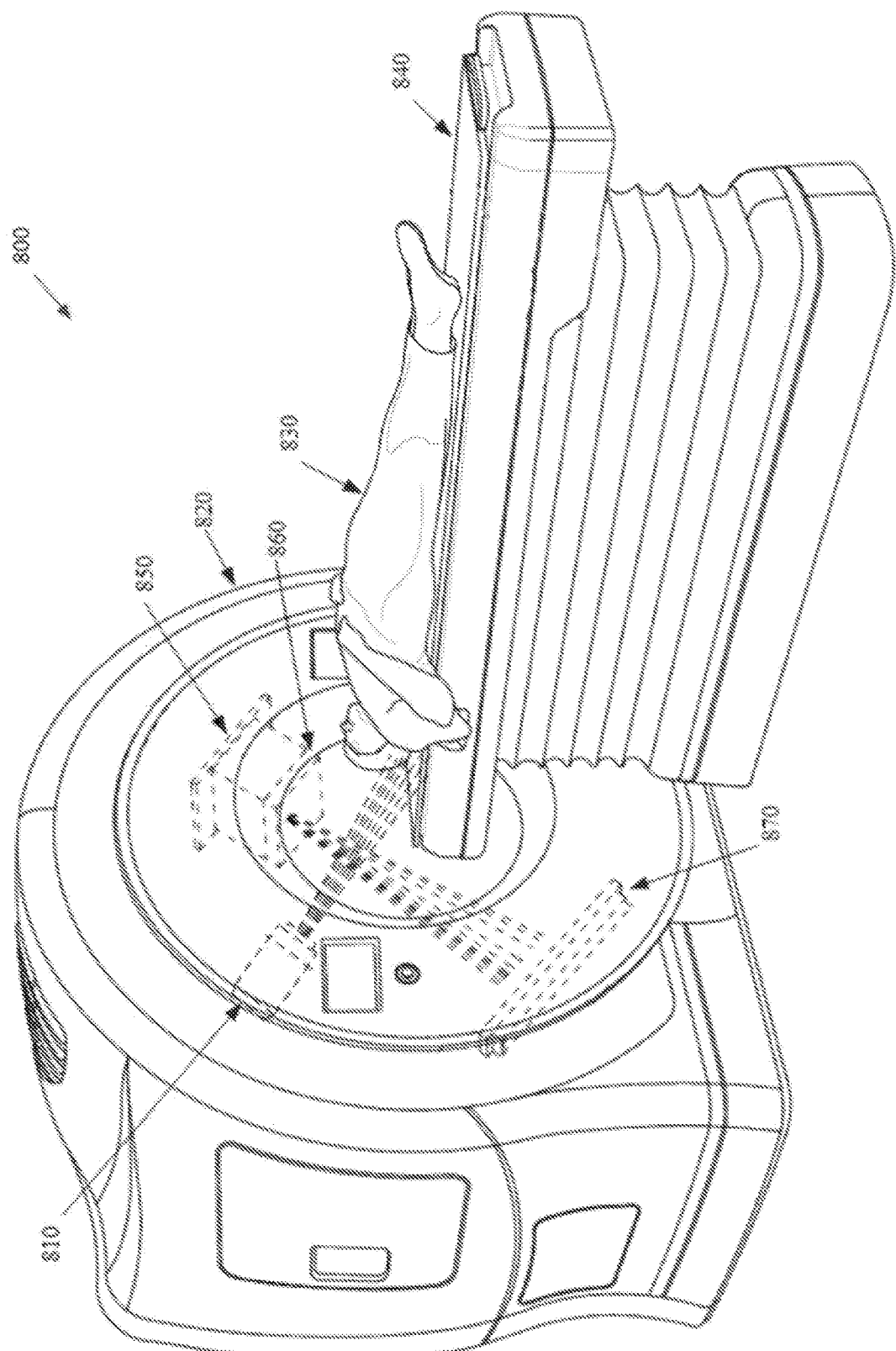
FIG. 1A illustrates a helical radiation delivery system, in accordance with embodiments described herein.

Described herein are embodiments for generating one or more three-dimensional (3D) images during therapeutic radiation beam delivery. A radiation delivery system may include one or more radiation sources that generate a therapeutic radiation beam to deliver a therapeutic dose of radiation to a target, such as a tumor, and one or more imaging radiation beams which are used to acquire imaging data associated with the target.

In a conventional radiation delivery system, a 3D volumetric image may be constructed of a volume of interest that includes the target. The volumetric image may be constructed by a processing device using a series of two-dimensional (2D) images that are captured before therapeutic radiation beam delivery has begun. For the purposes of this disclosure, a radiation treatment session may be defined as a period of time from when a patient enters a room to begin radiation treatment to when the patient leaves the room. Therapeutic radiation beam delivery may be defined as a period of time during which the therapeutic radiation beam is initially turned on to when the therapeutic radiation beam is finally turned off. In embodiments, the therapeutic radiation beam may be turned on and off during the period of time of therapeutic radiation beam delivery. Because the volumetric images are constructed using 2D images that were not acquired during therapeutic radiation beam delivery, the volumetric images may not accurately represent the volume of interest at the time of therapeutic radiation beam delivery. This may make it difficult to accurately track the motion of the target and estimate the therapeutic dose delivered to the target and/or other structures in proximity to the target, such as organs of a patient.

Aspects of the disclosure may remedy the above and other deficiencies by constructing volumetric images during therapeutic radiation beam delivery. Processing logic of a processing device of a radiation delivery system may initiate a radiation treatment session to deliver a therapeutic radiation beam to a target. During therapeutic radiation beam delivery, the processing logic may cause a radiation source to generate an imaging radiation beam through the target to one or more X-ray detectors to acquire imaging data associated with the target.

In some embodiments, the radiation delivery system may utilize a therapeutic radiation source to generate the therapeutic radiation beam and an imaging radiation beam. The imaging radiation beam may be used to acquire imaging data that may be used in conjunction with imaging data captured by an imaging system of the radiation delivery system. In some embodiments, one or more imaging radiation beam pulses may be interleaved between one or more therapeutic radiation beam pulses. For example, an imaging beam pulse may occur after two therapeutic radiation beam pulses or two imaging beam pulses may occur after one therapeutic radiation beam pulse. It should be noted that embodiments of the disclosure may utilize any number of imaging radiation beam pulses that are interleaved with any number of therapeutic radiation beam pulses. In an embodiment, the therapeutic radiation source may be used to simultaneously generate the therapeutic radiation beam and the imaging radiation beam, as will be described in further detail at FIG. 4 below.

In embodiments, the radiation delivery system may utilize multiple radiation sources. For example, the radiation delivery system may include a therapeutic radiation source and one or more X-ray radiation sources. In an embodiment, the one or more X-ray radiation sources may be offset relative to the therapeutic radiation source along an axis of rotation about the target. In some embodiments, an X-ray radiation source of the one or more X-ray radiation sources may be in alignment with the therapeutic radiation source to provide imaging data that corresponds to the perspective of the therapeutic radiation source.

The processing logic may utilize the imaging data acquired during therapeutic radiation beam delivery to construct one or more volumetric images. The volumetric images may correspond to a volume of interest that includes the target. In some embodiments, the processing logic may construct the volumetric images using less than a completely sampled set of imaging data. For example, the processing logic may utilize an image reconstruction algorithm to construct a volumetric image from a limited arc of imaging data. In another example, the processing logic may execute an iterative reconstruction algorithm to construct the most likely volumetric image from an under-sampled set of imaging data, which may not be in the form of continuous arcs. In some embodiments, the processing logic may utilize pre-treatment imaging data, planning time imaging data, or previously acquired imaging data in addition to the imaging data acquired during therapeutic radiation beam delivery to construct the volumetric image. In embodiments, pre-treatment imaging data may include imaging acquired before a radiation treatment session as well as imaging acquired during a radiation treatment session but before therapeutic radiation beam delivery. In some embodiments, the therapeutic radiation beam may also be used to acquire imaging data to be used in the construction of the volumetric images.

Constructing the volumetric images from imaging data that is acquired during therapeutic radiation beam delivery provides for an improved radiation delivery system. In embodiments, the volumetric images may be used to more accurately estimate a therapeutic dose delivered to the target or an object in proximity to the target (e.g., a radiation sensitive structure, such as an organ of a patient). In some embodiments, the volumetric images may be used to modify therapeutic radiation delivery to compensate for the motion or other visible change of the target, ensuring that the appropriate therapeutic dose is accurately delivered to the target.

FIG. 1A illustrates a helical radiation delivery system 800 in accordance with embodiments of the present disclosure. The helical radiation delivery system 800 may include a linear accelerator (LINAC) 850 mounted to a ring gantry 820. The LINAC 850 may be used to generate a radiation beam (i.e., treatment beam) by directing an electron beam towards an x-ray emitting target. The treatment beam may deliver radiation to a target region (i.e., a tumor). The treatment system further includes a multileaf collimator (MLC) 860 coupled with the distal end of the LINAC 850. The MLC includes a housing that houses multiple leaves that are movable to adjust an aperture of the MLC to enable shaping of the treatment beam. In embodiments, the MLC 860 may be a binary MLC that includes a plurality of leaves arranged in two opposing banks, where the leaves of the two opposing banks are interdigitated with one another and can be opened or closed to form an aperture. In some embodiments, the MLC 860 may be an electromagnetically-actuated MLC. In embodiments, MLC 860 may be any other type of MLC. The ring gantry 820 has a toroidal shape in which the patient 830 extends through a bore of the ring/toroid and the LINAC 850 is mounted on the perimeter of the ring and rotates about the axis passing through the center to irradiate a target region with beams delivered from one or more angles around the patient. During treatment, the patient 830 may be simultaneously moved through the bore of the gantry on a treatment couch 840.

The helical radiation delivery system 800 includes an imaging system, comprising the LINAC 850 as an imaging source and an x-ray detector 870. The LINAC 850 may be used to generate a mega-voltage x-ray image (MVCT) of a region of interest (ROI) of patient 830 by directing a sequence of x-ray beams at the ROI which are incident on the x-ray detector 870 opposite the LINAC 850 to image the patient 830 for setup and generate pre-treatment images. In one embodiment, the helical radiation delivery system 800 may also include a secondary imaging system consisting of a kV imaging source 810 mounted orthogonally relative to the LINAC 850 (e.g., separated by 90 degrees) on the ring gantry 820 and may be aligned to project an imaging x-ray beam at a target region and to illuminate an imaging plane of a detector after passing through the patient 130.

Figure 1B:
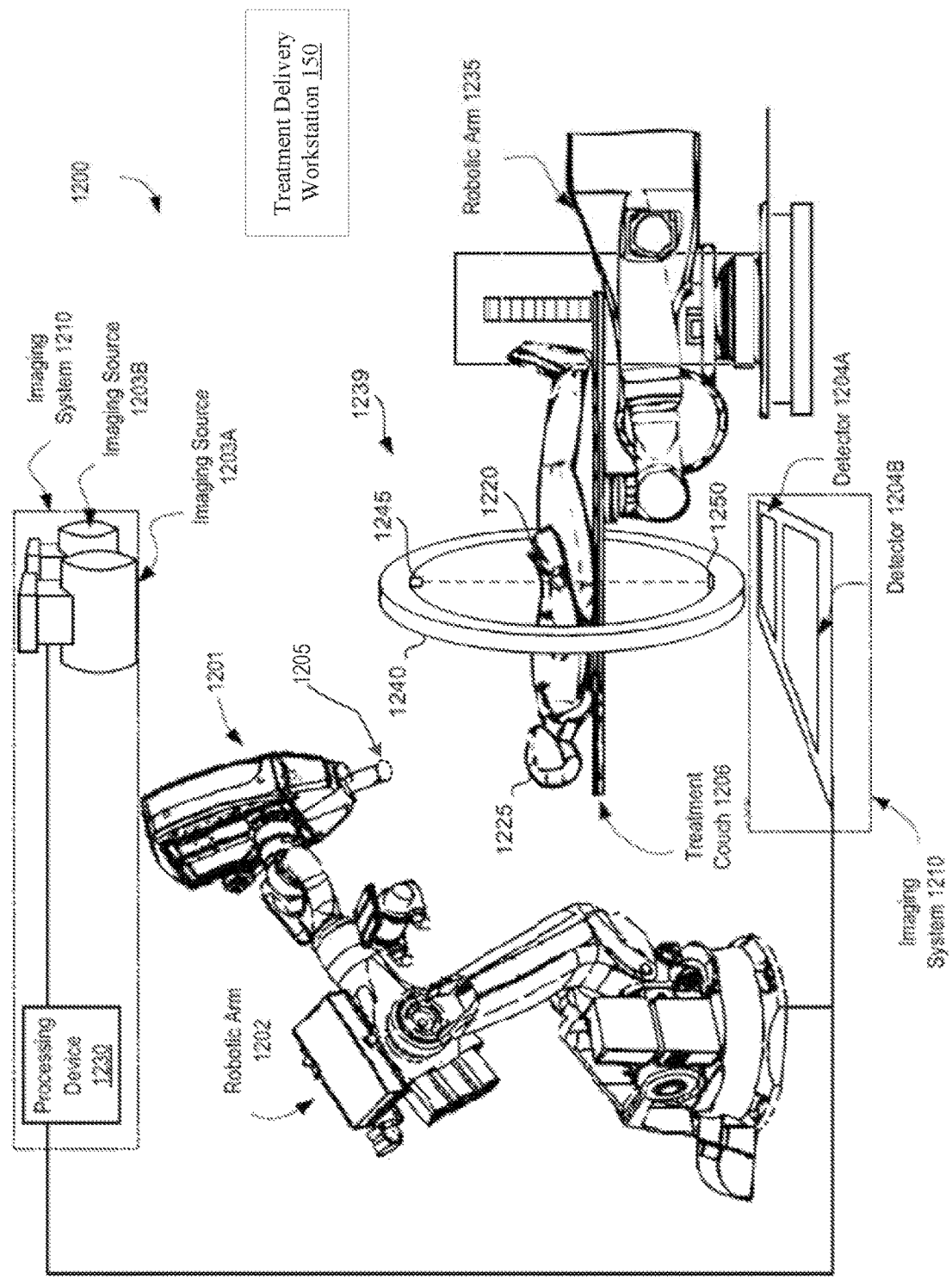
FIG. 1B illustrates a robotic radiation treatment system that may be used in accordance with embodiments described herein.

FIG. 1B illustrates a radiation treatment system 1200 that may be used in accordance with alternative embodiments described herein. As shown, FIG. 1B illustrates a configuration of a radiation treatment system 1200. In the illustrated embodiments, the radiation treatment system 1200 includes a linear accelerator (LINAC) 1201 that acts as a radiation treatment source and an MLC 1205 coupled with the distal end of the LINAC 1201 to shape the treatment beam. In one embodiment, the LINAC 1201 is mounted on the end of a robotic arm 1202 having multiple (e.g., 5 or more) degrees of freedom in order to position the LINAC 1201 to irradiate a pathological anatomy (e.g., target) with beams delivered from many angles, in many planes, in an operating volume around a patient. Treatment may involve beam paths with a single isocenter, multiple isocenters, or with a non-isocentric approach.

LINAC 1201 may be positioned at multiple different nodes (predefined positions at which the LINAC 1201 is stopped and radiation may be delivered) during treatment by moving the robotic arm 1202. At the nodes, the LINAC 1201 can deliver one or more radiation treatment beams to a target, where the radiation beam shape is determined by the leaf positions in the MLC 1205. The nodes may be arranged in an approximately spherical distribution about a patient. The particular number of nodes and the number of treatment beams applied at each node may vary as a function of the location and type of pathological anatomy to be treated.

In another embodiment, the robotic arm 1202 and LINAC 1201 at its end may be in continuous motion between nodes while radiation is being delivered. The radiation beam shape and 2-D intensity map is determined by rapid motion of the leaves in the MLC 1205 during the continuous motion of the LINAC 1201.

The radiation treatment system 1200 includes an imaging system 1210 having a processing device 1230 connected with x-ray sources 1203A and 1203B (i.e., imaging sources) and fixed x-ray detectors 1204A and 1204B. Alternatively, the x-ray sources 1203A, 1203B and/or x-ray detectors 1204A, 1204B may be mobile, in which case they may be repositioned to maintain alignment with the target, or alternatively to image the target from different orientations or to acquire many x-ray images and reconstruct a three-dimensional (3D) cone-beam CT. In one embodiment, the x-ray sources are not point sources, but rather x-ray source arrays, as would be appreciated by the skilled artisan. In one embodiment, LINAC 1201 serves as an imaging source, where the LINAC power level is reduced to acceptable levels for imaging.

Imaging system 1210 may perform computed tomography (CT) such as cone beam CT or helical megavoltage computed tomography (MVCT), and images generated by imaging system 1210 may be two-dimensional (2D) or three-dimensional (3D). The two x-ray sources 1203A and 1203B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 1206 during treatment) and to illuminate imaging planes of respective detectors 1204A and 1204B after passing through the patient. In one embodiment, imaging system 1210 provides stereoscopic imaging of a target and the surrounding volume of interest (VOI). In other embodiments, imaging system 1210 may include more or less than two x-ray sources and more or less than two detectors, and any of the detectors may be movable rather than fixed. In yet other embodiments, the positions of the x-ray sources and the detectors may be interchanged. In embodiments, the imaging data acquired from the fixed angles of by imaging system 1210 may be combined with prior images, such as a planning image or pre-treatment CT image. The imaging data acquired from the fixed angles acquired during therapeutic radiation beam delivery may be used to deform the prior images into a volumetric image representing the patient at the time of therapeutic radiation beam delivery. Detectors 1204A and 1204B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

In one embodiment, IGRT delivery system 1200 also includes a secondary imaging system 1239. Imaging system 1239 may be a Cone Beam Computed Tomography (CBCT) imaging system. Alternatively, other types of volumetric imaging systems may be used. The secondary imaging system 1239 includes a rotatable gantry 1240 (e.g., a ring) attached to an arm and rail system (not shown) that move the rotatable gantry 1240 along one or more axes (e.g., along an axis that extends from a head to a foot of the treatment couch 1206. An imaging source 1245 and a detector 1250 are mounted to the rotatable gantry 1240. The rotatable gantry 1240 may rotate 360 degrees about the axis that extends from the head to the foot of the treatment couch. Accordingly, the imaging source 1245 and detector 1250 may be positioned at numerous different angles. In one embodiment, the imaging source 1245 is an x-ray source and the detector 1250 is an x-ray detector. In one embodiment, the secondary imaging system 1239 includes two rings that are separately rotatable. The imaging source 1245 may be mounted to a first ring and the detector 1250 may be mounted to a second ring. In one embodiment, the rotatable gantry 1240 rests at a foot of the treatment couch during therapeutic radiation beam delivery to avoid collisions with the robotic arm 1202.

As shown in FIG. 1B, the image-guided radiation treatment system 1200 may further be associated with a treatment delivery workstation 150. The treatment delivery workstation may be remotely located from the radiation treatment system 1200 in a different room than the treatment room in which the radiation treatment system 1200 and patient are located. The treatment delivery workstation 150 may include a processing device (which may be processing device 1230 or another processing device) and memory that modify a treatment delivery to the patient 1225 based on a detection of a target motion that is based on one or more image registrations, as described herein.

Figure 1C:
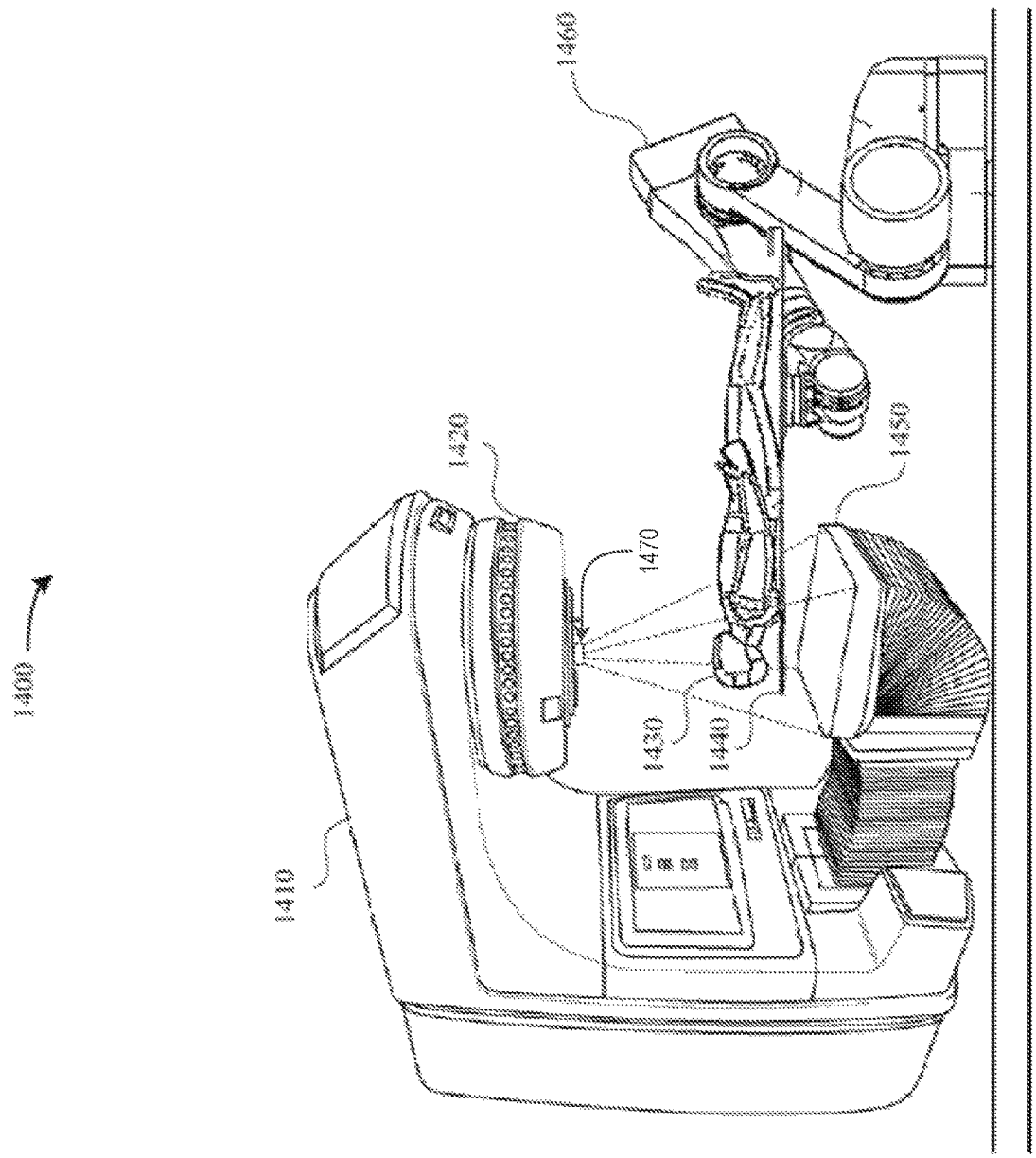
FIG. 1C illustrates a C-arm gantry-based radiation treatment system, in accordance with embodiments described herein.

FIG. 1C illustrates a C-arm radiation delivery system 1400. In one embodiment, in the C-arm system 1400 the beam energy of a LINAC may be adjusted during treatment and may allow the LINAC to be used for both x-ray imaging and radiation treatment. In another embodiment, the system 1400 may include an onboard kV imaging system to generate x-ray images and a separate LINAC to generate the higher energy therapeutic radiation beams. The system 1400 includes a C-arm gantry 1410, a LINAC 1420, an MLC 1470 coupled with the distal end of the LINAC 1420 to shape the beam, and a portal imaging detector 1450. The C-arm gantry 1410 may be rotated to an angle corresponding to a selected projection and used to acquire an x-ray image of a VOI of a patient 1430 on a treatment couch 1440. In embodiments that include a portal imaging system, the LINAC 1420 may generate an x-ray beam that passes through the target of the patient 1430 and are incident on the portal imaging detector 1450, creating an x-ray image of the target. After the x-ray image of the target has been generated, the beam energy of the LINAC 1420 may be increased so the LINAC 1420 may generate a radiation beam to treat a target region of the patient 1430. In another embodiment, the kV imaging system may generate an x-ray beam that passes through the target of the patient 1430, creating an x-ray image of the target. In some embodiments, the portal imaging system may acquire portal images during the delivery of a treatment. The portal imaging detector 1450 may measure the exit radiation fluence after the beam passes through the patient 1430. This may enable internal or external fiducials or pieces of anatomy (e.g., a tumor or bone) to be localized within the portal images.

Alternatively, the kV imaging source or portal imager and methods of operations described herein may be used with yet other types of gantry-based systems. In some gantry-based systems, the gantry rotates the kV imaging source and LINAC around an axis passing through the isocenter. In other embodiments, the kV imaging source and the LINAC may rotate independent of each other, while being able to image and deliver therapeutic radiation simultaneously to the same volume of interest. Gantry-based systems include ring gantries having generally toroidal shapes in which the patient's body extends through the bore of the ring/toroid, and the kV imaging source and LINAC are mounted on the perimeter of the ring and rotates about the axis passing through the isocenter. Gantry-based systems may further include C-arm gantries, in which the kV imaging source and LINAC are mounted, in a cantilever-like manner, over and rotates about the axis passing through the isocenter. In another embodiment, the kV imaging source and LINAC may be used in a robotic arm-based system, which includes a robotic arm to which the kV imaging source and LINAC are mounted as discussed above. Aspects of the present disclosure may further be used in other such systems such as a gantry-based LINAC system, static imaging systems associated with radiation therapy and radiosurgery, proton therapy systems using an integrated image guidance, interventional radiology and intraoperative x-ray imaging systems, etc.

Figure 2:
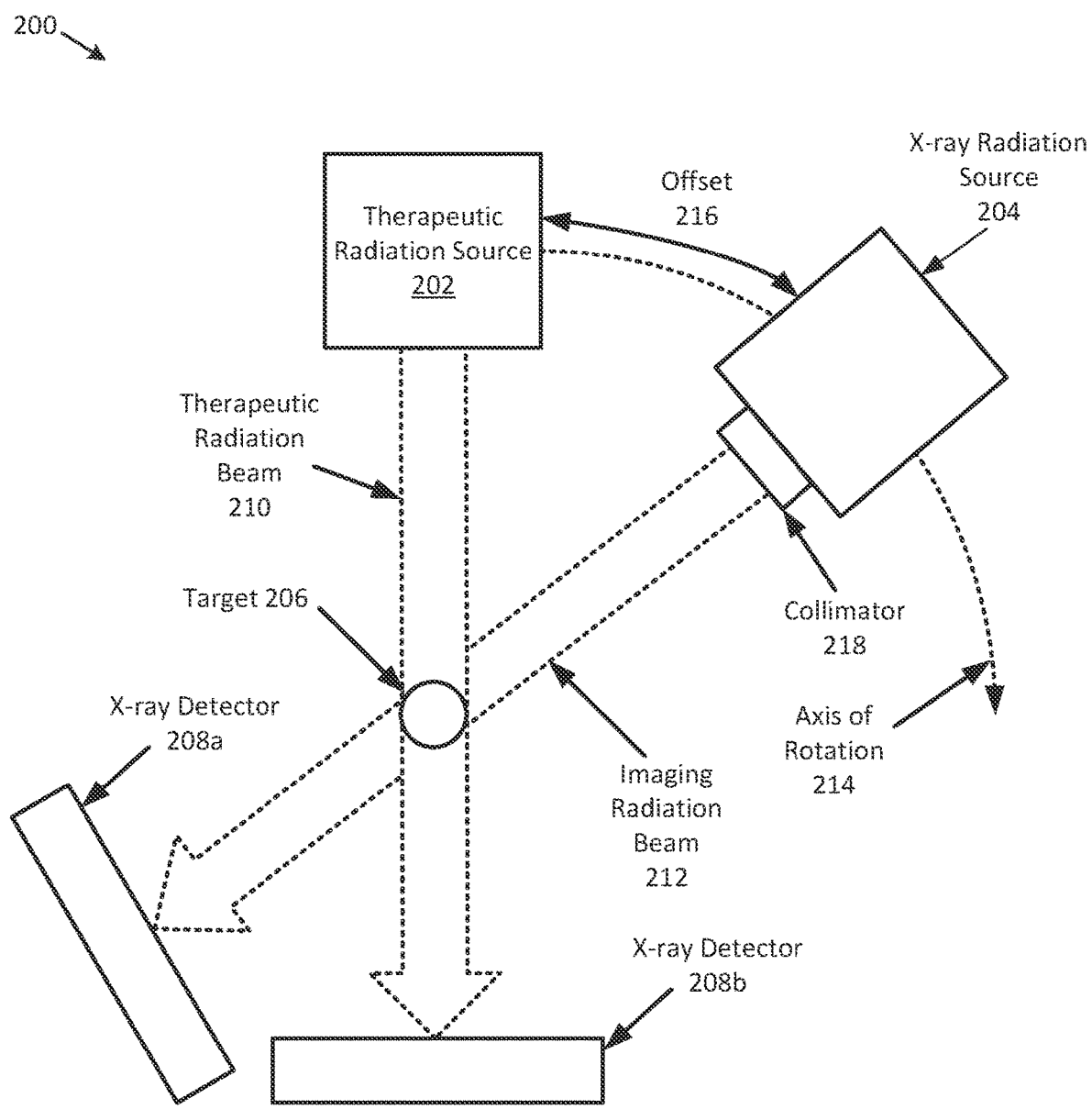
FIG. 2 is an illustration of an example of radiation delivery system acquiring imaging data using an X-ray radiation source during therapeutic radiation beam delivery, in accordance with embodiments of the disclosure.

FIG. 2 is an illustration of an example of radiation delivery system 200 acquiring imaging data using an X-ray radiation source during therapeutic radiation beam delivery, in accordance with embodiments of the disclosure. In embodiments, the radiation delivery system 200 may correspond to, and include the components of, one of the radiation delivery systems previously described at FIGS. 1A-C.

The radiation delivery system 200 includes a therapeutic radiation source 202 that generates a therapeutic radiation beam 210. In embodiments, the therapeutic radiation source 202 may correspond to LINAC 850 of FIG. 1A, LINAC 1201 of FIG. 1B, or LINAC 1420 of FIG. 1C. The radiation delivery system 200 includes an X-ray radiation source 204 that generates an imaging radiation beam 212. In embodiments, the X-ray radiation source 204 may correspond to kV imaging source 810 of FIG. 1A, one of imaging source 1203A or imaging source 1203B of FIG. 1B, or an imaging system of radiation delivery system 1400 of FIG. 1C. The radiation delivery system 200 further includes X-ray detector 208a and X-ray detector 208b. In embodiments, X-ray detector 208a and/or X-ray detector 208b may correspond to x-ray detector 870 of FIG. 1A, detector 1204A and detector 1204B of FIG. 1B, or an x-ray detector of radiation delivery system 1400 of FIG. 1C.

In embodiments, the X-ray radiation source 204 may be positioned at an offset 216 relative to the therapeutic radiation source 202 along an axis of rotation 214. The axis of rotation 214 may correspond to an axis upon which the X-ray radiation source 204 and/or the therapeutic radiation source 202 rotates about the target 206 during therapeutic radiation beam delivery. In an embodiment, the offset 216 may correspond to an angle between the therapeutic radiation source 202 and the X-ray radiation source 204. For example, the offset 216 may correspond to a 90-degree angle between the therapeutic radiation source 202 and the X-ray radiation source 204. In some embodiments, the X-ray radiation source 204 may be positioned in alignment with the therapeutic radiation source 202 and offset 216 may correspond to an axial offset of the X-ray radiation source 204 relative to the therapeutic radiation source 202. In embodiments, the axial offset may be between 0 and 40 centimeters (cm).

During therapeutic radiation beam delivery, the therapeutic radiation source 202 may generate a therapeutic radiation beam 210 to provide a dose of radiation to a target 206. In embodiments, the target 206 may correspond to a tumor or other structure being treated by the therapeutic radiation beam 210. While the therapeutic radiation beam 210 is active (e.g., at a same time), the X-ray radiation source 204 may generate the imaging radiation beam 212, which passes through the target 206 and is incident upon X-ray detector 208a to generate X-ray imaging data associated with the target 206.

In some embodiments, the X-ray radiation source 204 may include a collimator 218 that is used to shape the imaging radiation beam 212 to correlate to the shape of the target 206 or the shape of a volume of interest associated with the target 206. Shaping the imaging radiation beam 212 using the collimator 218 may improve the quality of the imaging data and reduce the imaging dose provided to a patient. In some embodiments, the collimator 218 may be an MLC, as previously described. In embodiments, the collimator 218 may be an iris collimator. In an embodiment, the collimator 218 may correspond to any type of collimator that may be used to shape the imaging radiation beam 212.

In embodiments, the therapeutic radiation beam 210 may be used to acquire imaging data in addition to the imaging radiation beam 212. In such an embodiment, a second detector (e.g., X-ray detector 208b) may be positioned opposite of target 206 relative to therapeutic radiation source 202. The therapeutic radiation beam 210 may pass through the target 206 and is incident upon X-ray detector 208b to generate additional X-ray imaging data associated with the target 206.

It should be noted that although radiation delivery system 200 is shown having a single therapeutic radiation source and a single x-ray radiation source, embodiments of the disclosure may utilize multiple X-ray radiation sources and/or therapeutic radiation sources. For example, a radiation delivery system may include a single therapeutic radiation source and multiple X-ray radiation sources positioned at various positions along the axis of rotation 214.

Figure 3A:
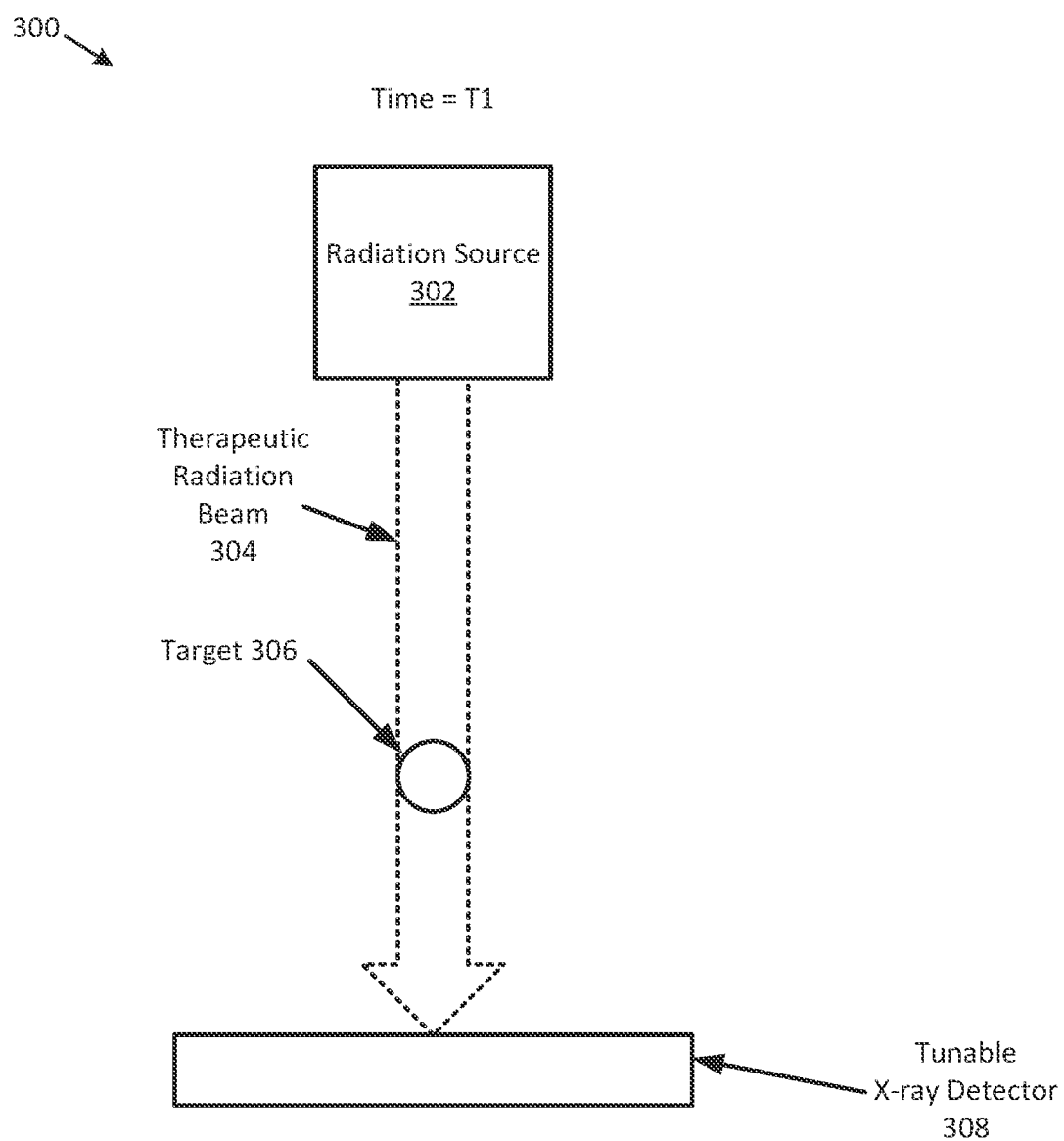
FIG. 3A is an illustration of an example of a radiation source of a radiation delivery system generating a therapeutic radiation beam at a first time, in accordance with embodiments of the disclosure.

FIG. 3A is an illustration of an example of a radiation source of a radiation delivery system 300 generating a therapeutic radiation beam at a first time, in accordance with embodiments of the disclosure. Radiation delivery system 300 may include similar components to the radiation delivery systems previously described at FIGS. 1A-2. The radiation delivery system 300 may utilize radiation source 302 to generate both a therapeutic radiation beam 304 and an imaging radiation beam (not shown). The imaging radiation beam may be used to acquire imaging data that is used in conjunction with imaging data that is acquired using one or more X-ray radiation sources (not shown), as will be described at FIG. 3B below. In an embodiment, the radiation source 302 may interleave one or more pulses of a therapeutic radiation beam 304 with one or more pulses of an imaging radiation beam during radiation therapy delivery. In other embodiments, the radiation source 302 may simultaneously generate a therapeutic radiation beam 304 and an imaging beam, as will be described in more detail at FIG. 4 below.

In embodiments, the radiation delivery system 300 may include a tunable X-ray detector 308. The tunable X-ray detector 308 may be selectively tuned to detect radiation beams within a particular range of energy levels. For example, if the therapeutic radiation beam 304 is a mega electron-volt (MeV) radiation beam and the imaging radiation beam is a kiloelectron volt (KeV) radiation beam, then the tunable X-ray detector 308 may be selectively tuned to detect radiation beams in the KeV range of energy levels.

Referring to FIG. 3A, the radiation source 302 is generating one or more therapeutic radiation beam 304 pulses at a first time (T1) to provide a therapeutic dose of radiation to the target 306. In some embodiments, the therapeutic radiation beam 304 may be used to generate imaging data, as previously described at FIG. 2. In such an embodiment, the tunable X-ray detector 308 may be tuned to detect radiation beams that correspond to the energy level of the therapeutic radiation beam 304 to generate imaging data when the therapeutic radiation beam 304 is incident upon the tunable X-ray detector 308. For example, the tunable X-ray detector 308 may be tuned to detect MeV radiation beams.

Figure 3B:
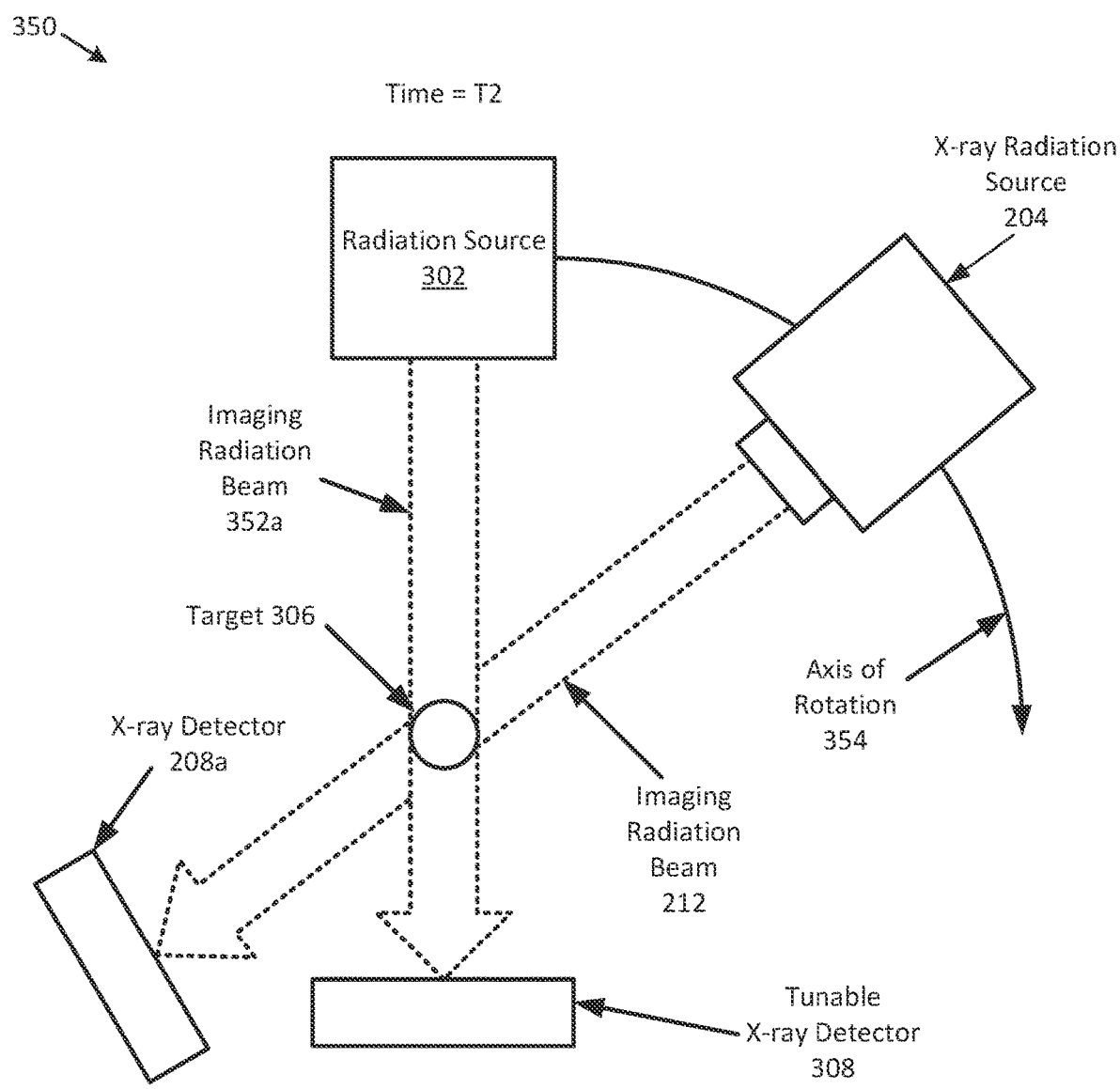
FIG. 3B is an illustration of an example of a radiation source of a radiation delivery system generating an imaging radiation beam at a second time, in accordance with embodiments of the disclosure.

FIG. 3B is an illustration of an example of a radiation source of a radiation delivery system 350 generating an imaging radiation beam at a second time, in accordance with embodiments of the disclosure. Radiation delivery system 350 may include similar components to the radiation delivery systems previously described at FIGS. 1A-3A. Radiation delivery system 350 further includes X-ray radiation source 204 generating an imaging radiation beam 212 that passes through target 306 and is incident upon X-ray detector 208a to acquire imaging data associated with the target 306, as previously described at FIG. 2.

Referring to FIG. 3B, the radiation source 302 is generating one or more imaging radiation beam 352 pulses at a second time (T2) to acquire imaging data associated with the target 306. While the radiation source 302 is generating the one or more imaging radiation beam 352 pulses, the tunable X-ray detector 308 may be tuned to detect radiation beams that correspond to the energy level of the imaging radiation beam 352 to generate the imaging data when the imaging radiation beam 352 is incident upon the tunable X-ray detector 308. For example, the tunable X-ray detector 308 may be tuned to detect kV radiation beams. In embodiments, the imaging radiation beam 352 pulses may be active in one or more contiguous arcs to acquire imaging data associated with the target 306.

In embodiments, the process of interleaving therapeutic radiation beam pulses and imaging radiation beam pulses as previously described at FIGS. 3A and 3B may be iteratively performed as the radiation source 302 travels along the axis of rotation 354 about target 306 during therapeutic radiation beam delivery.

Figure 4:
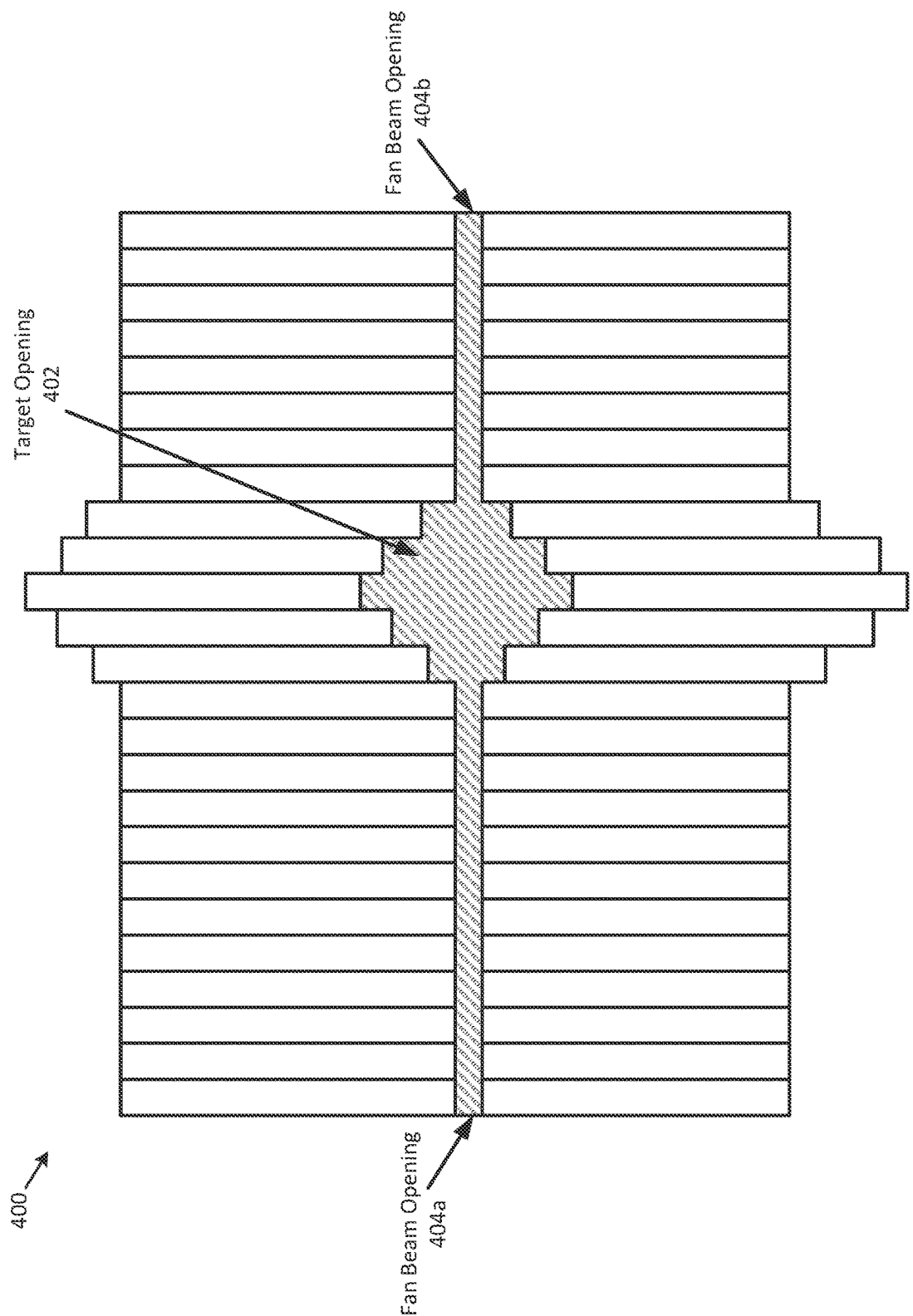
FIG. 4 is an illustration of an example of a multi-leaf collimator forming a target opening and a fan beam opening, in accordance with embodiments of the disclosure.

FIG. 4 is an illustration of an example of a multi-leaf collimator 400 forming a target opening and a fan beam opening, in accordance with embodiments of the disclosure. Multi-leaf collimator (MLC) 400 may be used to perform dynamic source collimation of a radiation beam in the treatment plane to enable fan-beam computed tomography (CT) by placement of fan beam opening 404a and fan beam opening 404b within, or adjacent to, the treatment opening 402. Fan beam opening 404a and fan beam opening 404b may be sized and positioned such that the imaging data encompasses a treatment field of the target during an acquisition interval.

In embodiments, the leaves of MLC 400 may support an imaging mode during therapeutic radiation beam delivery in which all normally-closed leaves in a projection are positioned with a sliver aperture to form fan beam opening 404a and fan beam opening 404b. Fan beam opening 404a and fan beam opening 404b may allow a small amount of fluence through a narrow collimation to shape a radiation beam into a fan beam to acquire imaging data associated with a target, while treatment opening 402 may shape the radiation beam to provide a therapeutic dose of radiation to the target. In some embodiments, fan beam opening 404a and fan beam opening 404b may be positioned such that the fan beam imaging data is longitudinally centered across the treatment field. MLC 400 may enable a radiation source, such as radiation source 302 of FIGS. 3A and 3B, to simultaneously generate a therapeutic radiation beam and an imaging radiation beam by having the target opening 402 be the union for therapeutic radiation and fan beam openings 404a, b for imaging.

In embodiments, to reduce leakage for closed leaves, or to reduce dosage through sliver-opened leaves, the mating faces of the leaf pairs may be angled or toothed to provide tunable attenuation over a small range of nearly-closed leaf windows. Narrow leaf windows near the edge of the treatment field may already have attenuation due to the angle between the beam and vertical leaf faces. Accordingly, the sliver width may be a function of the offset from the center.

In some embodiments, a sliding imaging aperture may be used to acquire a circular trajectory of a plane of interest. The imaging aperture may slide at the speed of a treatment couch of a radiation delivery system, but in the opposite direction. The spacing of imaging slices acquire may depend on the duration of the scan, the speed of the treatment couch, and the recovery speed at which the aperture may be reset to the leading edge.

Figure 5:
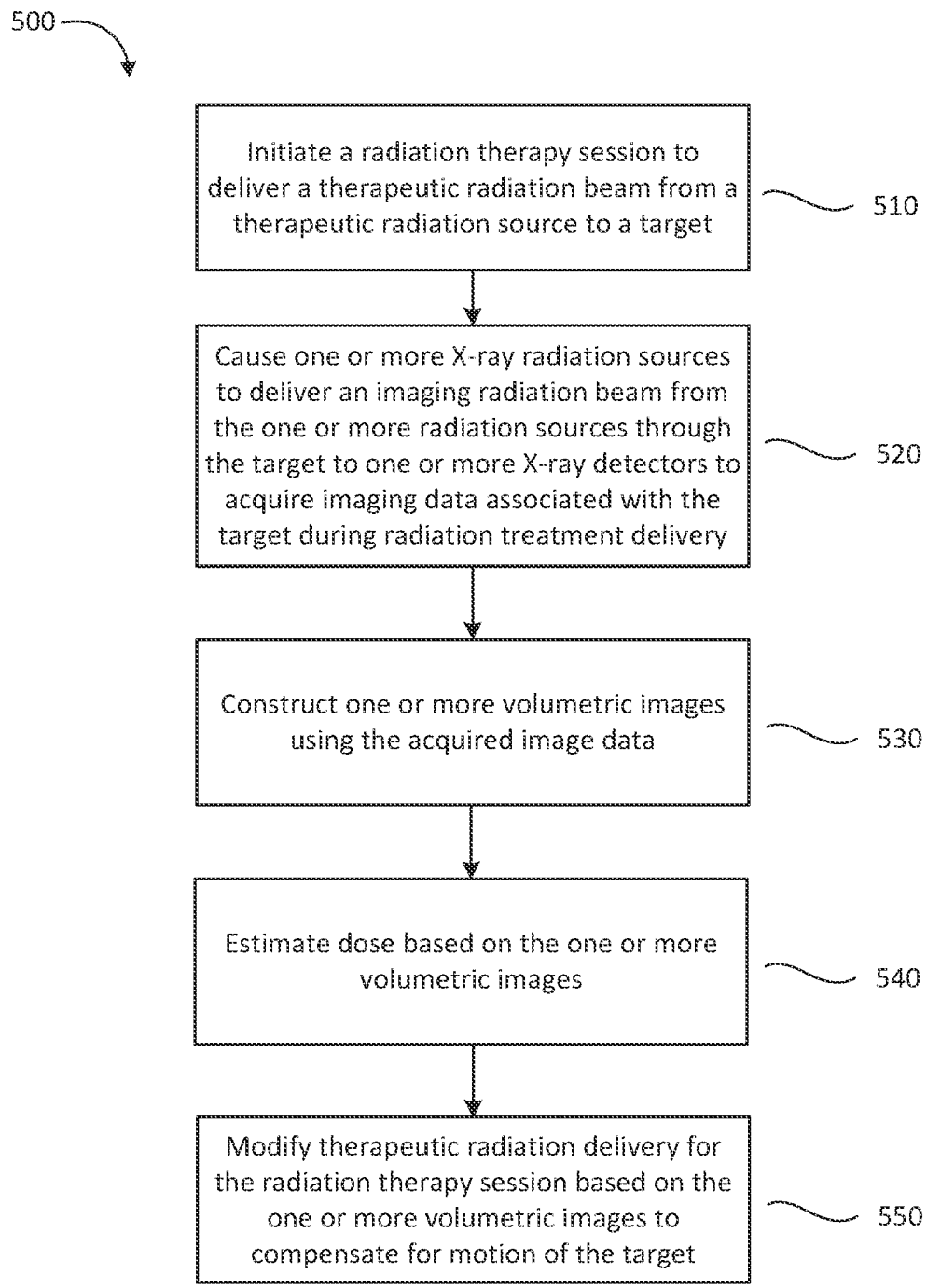
FIG. 5 depicts a flow diagram of a method of constructing volumetric images using imaging data acquired during therapeutic radiation beam delivery, in accordance with embodiments of the disclosure.

FIG. 5 depicts a flow diagram of a method 500 of constructing volumetric images using imaging data acquired during therapeutic radiation beam delivery, in accordance with embodiments of the disclosure. Method 500 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In embodiments, various portions of method 500 may be performed by processing logic of a processing device of a radiation delivery system as previously described at FIGS. 1A-4.

With reference to FIG. 5, method 500 illustrates example functions used by various embodiments. Although specific function blocks ("blocks") are disclosed in method 500, such blocks are examples. That is, embodiments are well suited to performing various other blocks or variations of the blocks recited in method 500. It is appreciated that the blocks in method 500 may be performed in an order different than presented, and that not all of the blocks in method 500 may be performed.

Method 500 begins at block 510, where the processing logic initiates a radiation treatment session to deliver a therapeutic radiation beam from a therapeutic radiation source to a target.

At block 520, the processing logic causes one or more X-ray radiation sources to delivery an imaging radiation beam from the one or more X-ray radiation sources through the target to one or more X-ray detectors to acquire imaging data associated with the target during therapeutic radiation beam delivery, as previously described at FIGS. 2-4.

At block 530, the processing logic constructs one or more volumetric images using the acquired image data. In some embodiments, the processing logic may construct the volumetric images using less than a completely sampled set of imaging data. In embodiments, the processing logic may utilize pre-treatment imaging data, planning time imaging data, previously acquired imaging data in addition to the imaging data acquired during therapeutic radiation beam delivery to construct the volumetric image.

At block 540, the processing logic estimates a therapeutic dose of radiation based on the one or more volumetric images. In embodiments, the processing logic may estimate the therapeutic dose provided to the target by the therapeutic radiation beam and/or the imaging radiation beam. For example, the processing logic may estimate the therapeutic dose provided to a tumor of a patient. In some embodiments, the processing logic may estimate the therapeutic dose provided to an object in proximity to the target by the therapeutic radiation beam and/or imaging radiation beam. For example, the processing logic may estimate the therapeutic dose provided to an organ of a patient that is in proximity to the tumor.

At block 550, the processing logic modifies therapeutic radiation delivery for the radiation treatment session based on the one or more volumetric images to compensate for motion of the target. In embodiments, the processing logic may modify the therapeutic radiation delivery by causing a shape of an aperture or opening of a collimator, such as target opening 402 of FIG. 4, to be modified to correlate to the shape and/or position of the target due to the motion of the target. In some embodiments, the processing logic may modify the radiation treatment session by modifying times when the therapeutic radiation beam and/or imaging radiation beam are active during the radiation treatment session. In an embodiment, the processing logic may modify the radiation treatment session by modifying an energy level of the therapeutic radiation beam and/or imaging radiation beam. In embodiments, the processing logic may modify the radiation treatment session by modifying the position of the one or more radiation sources relative to target along an axis of rotation. In an embodiment, the processing logic may modify the shape of the therapeutic radiation beam's collimator aperture to avoid organs at risk, such as if an organ at risk moves between the therapeutic radiation source and the target. In some embodiments, the processing logic may modify other parameters associated with a radiation delivery system to compensate for motion of the target.

Figure 6:
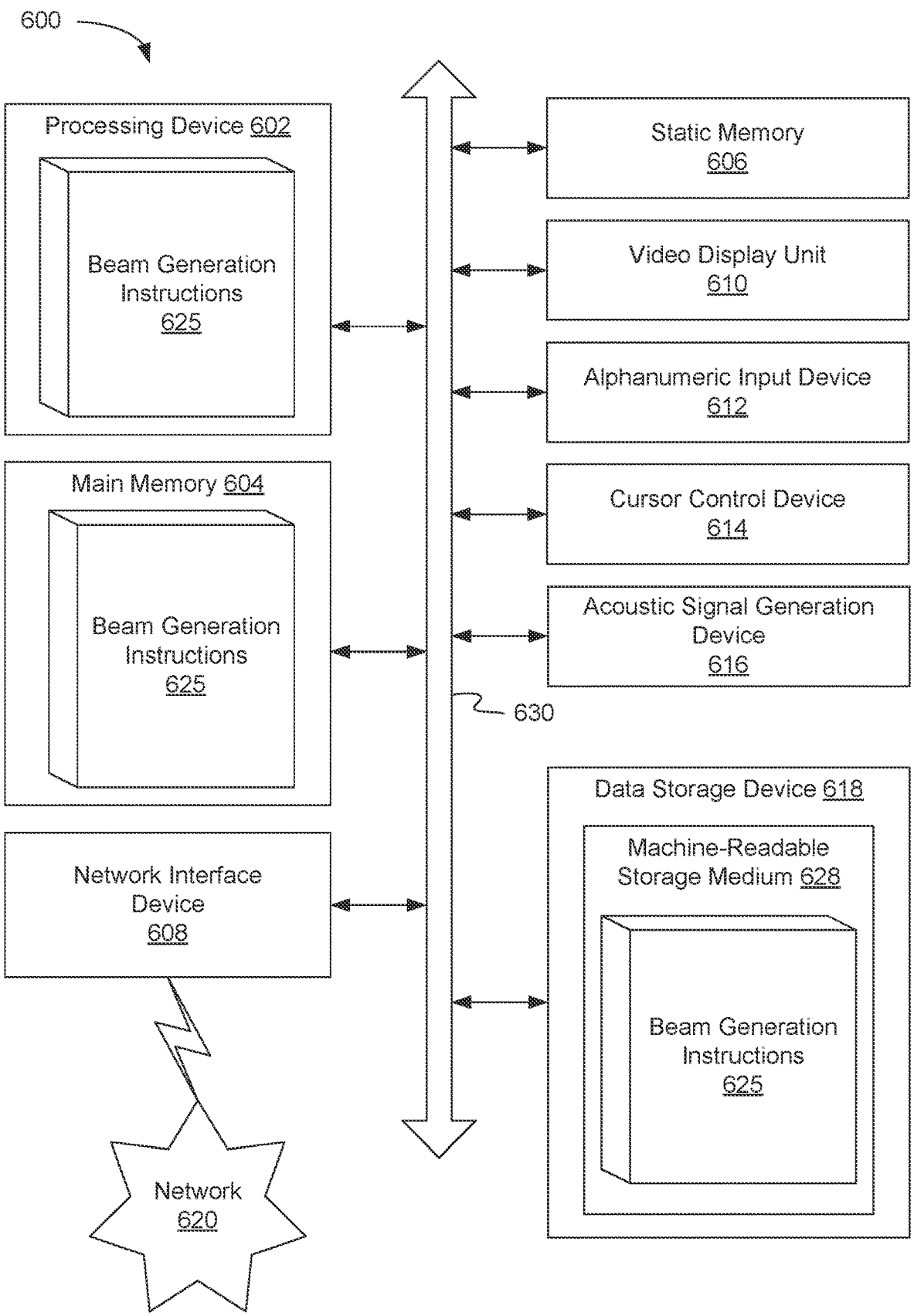
FIG. 6 is a block diagram of an example computing device that may perform one or more of the operations described herein, in accordance with some embodiments.

FIG. 6 is a block diagram of an example computing device 600 that may perform one or more of the operations described herein, in accordance with some embodiments. Computing device 600 may be connected to other computing devices in a LAN, an intranet, an extranet, and/or the Internet. The computing device may operate in the capacity of a server machine in client-server network environment or in the capacity of a client in a peer-to-peer network environment. The computing device may be provided by a personal computer (PC), a set-top box (STB), a server, a network router, switch or bridge, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein.

The example computing device 600 may include a processing device (e.g., a general purpose processor, a PLD, etc.) 602, a main memory 604 (e.g., synchronous dynamic random access memory (DRAM), read-only memory (ROM)), a static memory 606 (e.g., flash memory and a data storage device 618), which may communicate with each other via a bus 630.

Processing device 602 may be provided by one or more general-purpose processing devices such as a microprocessor, central processing unit, or the like. In an illustrative example, processing device 602 may comprise a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing device 602 may also comprise one or more special-purpose processing devices such as an application specific integrated circuit (ASIC), a field programmable gate array (FPGA), a digital signal processor (DSP), network processor, or the like. The processing device 602 may be configured to execute the operations described herein, in accordance with one or more aspects of the present disclosure, for performing the operations and steps discussed herein.

Computing device 600 may further include a network interface device 608 which may communicate with a network 620. The computing device 600 also may include a video display unit 610 (e.g., a liquid crystal display (LCD) or a cathode ray tube (CRT)), an alphanumeric input device 612 (e.g., a keyboard), a cursor control device 614 (e.g., a mouse) and an acoustic signal generation device 616 (e.g., a speaker). In one embodiment, video display unit 610, alphanumeric input device 612, and cursor control device 614 may be combined into a single component or device (e.g., an LCD touch screen).

Data storage device 618 may include a computer-readable storage medium 628 on which may be stored one or more sets of instructions that may include beam generation instructions 625 for carrying out the operations described herein, in accordance with one or more aspects of the present disclosure. The instructions may also reside, completely or at least partially, within main memory 604 and/or within processing device 602 during execution thereof by computing device 600, main memory 604 and processing device 602 also constituting computer-readable media. The instructions may further be transmitted or received over a network 620 via network interface device 608.

While computer-readable storage medium 628 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding or carrying a set of instructions for execution by the machine and that cause the machine to perform the methods described herein. The term "computer-readable storage medium" shall accordingly be taken to include, but not be limited to, solid-state memories, optical media and magnetic media.

It should be noted that the methods and apparatus described herein are not limited to use only with medical diagnostic imaging and treatment. In alternative implementations, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Reference throughout this specification to "one embodiment" or "an embodiment" means that a particular feature, structure, or characteristic described in connection with the embodiments included in at least one embodiment. Thus, the appearances of the phrase "in one embodiment" or "in an embodiment" in various places throughout this specification are not necessarily all referring to the same embodiment.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

What is claimed is:

1. An X-ray imaging and radiation delivery system, comprising:
   a therapeutic X-ray source to create a therapeutic X-ray beam;
   one or more X-ray imaging sources to create one or more imaging X-ray beams, wherein the one or more X-ray imaging sources and the therapeutic X-ray source are positioned to simultaneously direct the therapeutic X-ray beam and the one or more imaging X-ray beams to a target; and
   a processing device, operatively coupled to the therapeutic X-ray source and the one or more X-ray imaging sources, to:
      turn on the therapeutic X-ray beam to initiate a radiation treatment session and deliver the therapeutic X-ray beam from the therapeutic X-ray source to theft target as the therapeutic X-ray source travels about the target;
      turn off the therapeutic X-ray beam to end the radiation treatment session;
      acquire, during the radiation treatment session, imaging data associated with the target by causing the one or more X-ray imaging sources to deliver the one or more imaging X-ray beams through the target to one or more X-ray detectors; and
      construct one or more volumetric images using the imaging data.

2. The radiation delivery system of claim 1, wherein delivery of the one or more imaging X-ray beams is after turning on the therapeutic X-ray beam and before turning off the therapeutic X-ray beam.

3. The radiation delivery system of claim 1, wherein delivery of the one or more imaging X-ray beams is concurrent with delivery of the therapeutic X-ray beam.

4. The radiation delivery system of claim 3, wherein the processing device further causes the therapeutic X-ray source to deliver the one or more imaging X-ray beams within a same interval as delivery of the therapeutic X-ray beam.

5. The radiation delivery system of claim 1, wherein delivery of the one or more imaging X-ray beams is interleaved with delivery of the therapeutic X-ray beam.

6. The radiation delivery system of claim 5, wherein the therapeutic X-ray beam is active between one or more pulses of the one or more imaging X-ray beams, and wherein construction of the one or more volumetric images is based on the imaging data acquired from the one or more pulses of the one or more imaging X-ray beams.

7. The radiation delivery system of claim 1, wherein the therapeutic X-ray source includes a LINAC X-ray source, and wherein the processing device is further to acquire, during the radiation treatment session, imaging data associated with the target by causing the LINAC X-ray source to deliver a MV imaging beam of the one or more imaging X-ray beams through the target to the one or more X-ray detectors.

8. The radiation delivery system of claim 1, wherein the one or more X-ray detectors are tunable to selectively detect the one or more imaging X-ray beams.

9. The radiation delivery system of claim 1, wherein the one or more volumetric images are constructed using less than a completely sampled set of imaging data.

10. The radiation delivery system of claim 1, wherein the processing device is further to cause a multi-leaf collimator to form an opening that comprises a union of a first opening to shape the therapeutic X-ray beam to correspond to the target and a second opening to shape the one or more imaging X-ray beams into a fan beam to acquire the imaging data.

11. The radiation delivery system of claim 1, wherein the processing device is further to estimate a therapeutic dose delivered to one or more of the target or an object in proximity to the target based on the one or more volumetric images.

12. The radiation delivery system of claim 1, wherein the processing device is further to modify therapeutic radiation delivery for the radiation treatment session based on the one or more volumetric images.

13. A method comprising:
   turning on, by a processing device of an X-ray imaging and radiation delivery system, a therapeutic X-ray beam to initiate a radiation treatment session and deliver the therapeutic X-ray beam from a therapeutic X-ray source to a target as the therapeutic X-ray source travels about the target;
   turning off, by the processing device, the therapeutic X-ray beam to end the radiation treatment session;
   acquiring, by the processing device during the radiation treatment session, imaging data associated with the target by causing one or more X-ray imaging sources to deliver one or more imaging X-ray beams through the target to one or more X-ray detectors, wherein the one or more X-ray imaging sources and the therapeutic X-ray source are positioned to simultaneously direct the therapeutic X-ray beam and the one or more imaging X-ray beams to the target; and
   constructing, by the processing device, one or more volumetric images using the imaging data.

14. The method of claim 13, wherein delivery of the one or more imaging X-ray beams is after turning on the therapeutic X-ray beam and before turning off the therapeutic X-ray beam.

15. The method of claim 13, wherein delivery of the one or more imaging X-ray beams is concurrent with delivery of the therapeutic X-ray beam.

16. The method of claim 13, wherein delivery of the one or more imaging X-ray beams is interleaved with delivery of the therapeutic X-ray beam.

17. A non-transitory computer-readable storage medium including instructions which, when executed by a processing device of an X-ray imaging and therapy system, cause the processing device to:
   turn on a therapeutic X-ray beam to initiate a radiation treatment session and deliver the therapeutic X-ray beam from a therapeutic X-ray source to a target as the therapeutic X-ray source travels about the target;
   turn off the therapeutic X-ray beam to end the radiation treatment session;
   acquire, during the radiation treatment session, imaging data associated with the target by causing one or more X-ray imaging sources to deliver one or more imaging X-ray beams through the target to one or more X-ray detectors, wherein the one or more X-ray imaging sources and the therapeutic X-ray source are positioned to simultaneously direct the therapeutic X-ray beam and the one or more imaging X-ray beams to the target; and
   construct one or more volumetric images using the imaging data.

18. The non-transitory computer-readable storage medium of claim 17, wherein delivery of the one or more imaging X-ray beams is after turning on the therapeutic X-ray beam and before turning off the therapeutic X-ray beam.

19. The non-transitory computer-readable storage medium of claim 17, wherein delivery of the one or more imaging X-ray beams is concurrent with delivery of the therapeutic X-ray beam.

20. The non-transitory computer-readable storage medium of claim 17, wherein delivery of the one or more imaging X-ray beams is interleaved with delivery of the therapeutic X-ray beam.

* * * * *